United States Patent [19]

Baisden

[11] Patent Number: 4,767,717

[45] Date of Patent: Aug. 30, 1988

[54] METHOD OF DETECTING AND QUANTITATING CELL MALIGNANCY IN BIOLOGICAL TISSUE

[76] Inventor: C. Robert Baisden, 3227 Ramsgate Rd., Augusta, Ga. 30909

[21] Appl. No.: 729,621

[22] Filed: May 2, 1985

[51] Int. Cl.$^4$ .............................................. G01N 33/48
[52] U.S. Cl. ...................... 436/64; 128/653; 250/373; 356/51; 424/3; 435/173; 436/63; 436/164
[58] Field of Search ...................... 435/1, 173; 436/63, 436/64, 164, 805; 250/372, 373, 461.2; 128/653; 356/51; 424/3

[56] References Cited

U.S. PATENT DOCUMENTS

| | | |
|---|---|---|
| 2,708,515 | 5/1955 | Bliss .................................... 209/111 |
| 3,327,117 | 6/1967 | Kamentsky ........................ 250/461.2 |
| 3,327,119 | 6/1967 | Kamentsky .......................... 128/653 |
| 3,456,641 | 7/1969 | Yokota et al. .......................... 128/4 |
| 3,463,142 | 8/1969 | Harte ..................................... 128/2 |
| 3,497,690 | 2/1970 | Wheeless, Sr. et al. .............. 250/71 |
| 3,505,524 | 4/1970 | Hjerten ............................... 250/83.3 |
| 3,540,824 | 10/1968 | Fonda et al. .......................... 356/53 |
| 3,613,884 | 10/1971 | Van Gaalen ...................... 209/111.6 |
| 3,694,086 | 9/1972 | May ................................... 250/373 |
| 3,699,336 | 10/1972 | Ehrlich et al. ..................... 250/83.3 |
| 3,740,144 | 6/1973 | Walker ................................. 356/53 |
| 3,765,775 | 10/1973 | Ganssle et al. ..................... 356/188 |
| 3,824,393 | 7/1974 | Brain .............................. 250/222 PC |
| 3,861,788 | 1/1975 | Webster .............................. 350/315 |
| 3,877,818 | 4/1975 | Button et al. ...................... 356/186 |
| 4,006,360 | 2/1977 | Mueller .............................. 250/373 |
| 4,017,192 | 4/1977 | Rosenthal .......................... 356/201 |
| 4,063,892 | 12/1977 | Vassileu et al. .................... 23/230 B |
| 4,093,381 | 6/1978 | Karamian ............................ 356/51 |
| 4,115,802 | 9/1978 | Kramer et al. ...................... 358/93 |
| 4,195,225 | 3/1980 | Karamian ........................... 250/373 |
| 4,207,892 | 6/1980 | Binder ................................ 128/665 |
| 4,293,221 | 10/1981 | Kay et al. ........................... 356/318 |
| 4,350,892 | 9/1982 | Kay et al. ......................... 250/461.2 |

OTHER PUBLICATIONS

Mellors et al (1952), Science, vol. 116, pp. 265–269.
Zworykin et al (1957), Science, vol. 126, No. 3278, pp. 805–810.
Mellors (1950), Science, vol. 112, pp. 381–389.

*Primary Examiner*—Sidney Marantz
*Attorney, Agent, or Firm*—Morton J. Rosenberg

[57] ABSTRACT

A method of detecting and quantitating cell malignancy in biological tissue is provided and initially includes preparing a tissue sample having a substantially constant thickness. The tissue sample was impinged by filtered electromagnetic energy within an approximate bandwidth between 255.0–265.0 nm with a preferred wavelength of 260.0 nm. A standard Zeiss microscope was used to observe and measure the nuclear material with the microscope being fitted with quartz optics. The volume of nuclear material being examined was maintained relatively constant by selecting an aperture smaller in diameter than the magnified image of the nucleus being examined in combination with the subtantially uniform thickness of the tissue samples. The electromagnetic energy subsequent to being reflected from the tissue sample was passed through a second optical filter having an approximate filtering capacity in the range of 260.0 nm. The amount of electromagnetic energy within the predetermined bandwidth determined by the filters and absorbed by the nucleate of the cells within the tissue sample was measured. The amount of electromagnetic energy within the predetermined bandwidth absorbed by the nucleate was then quantified showing a higher absorptance of the filtered electromagnetic energy by malignant cells when taken with respect to normal cells.

15 Claims, No Drawings

METHOD OF DETECTING AND QUANTITATING CELL MALIGNANCY IN BIOLOGICAL TISSUE

BACKGROUND OF THE INVENTION

1. Field of the Invention

The subject invention directs itself to an improved method of detecting and quantitating cell malignancy in biological tissue. In particular, the subject invention directs itself to a method of measuring the amount of electromagnetic energy at approximately 260.0 nm which is absorbed by the nucleate of tissue samples. More in particular, the inventive method pertains to a system wherein the volume of nuclear material is controlled during the measuring of the amount of electromagnetic energy absorbed by the nucleate of the cells. Further, the inventive method relates to selecting a microscope aperture smaller in diameter than the magnified image of the nucleus being examined and by sectioning the tissue samples to a substantially uniform thickness. Still further, the invention herein described is directed to impinging the tissue samples with electromagnetic energy at approximately 260.0 nm and further filtering the reflected energy from the tissue samples with a secondary filter having a filtering capacity at approximately 260.0 nm prior to measurement of the electromagnetic energy from the tissue sample.

2. Prior Art

Methods of detecting cell malignancy in biological tissue are well-known in the art. Prior art known to the Applicant includes U.S. Pat. Nos. #3,327,117; #3,327,119; #4,207,892; #4,195,225; #4,115,802; #4,017,192; #3,505,524; #3,456,641; #3,824,393; #3,699,336; #3,740,144; #3,861,788; #3,765,775; #3,613,884; #3,540,824; #4,350,892; #4,293,221; #3,463,142; #3,497,690; #2,708,515; #4,093,381; #3,877,818; and, #4,063,892.

U.S. Pat. #3,327,117 and #3,327,119 are directed to cancer cell methods and apparatus. However, in such prior art, an aperture and optical path length was used which was large enough to contain the entire cell whose absorptance was being measured. In such prior art, the volume of the cell nucleus influenced the amount of absorptance at 260.0 nm. By allowing the volume of the cell nucleus to influence the amount of absorptance, such increases the uncertain parameters and diminishes the correlation between different growth patterns and the 260.0 nm wavelength absorptance of the genetic material.

SUMMARY OF THE INVENTION

A method of detecting cell malignancy in tissue including the initial step of providing a tissue sample. The tissue sample was impinged with electromagnetic energy within a predetermined electromagnetic energy bandwidth. The amount of electromagnetic energy within the predetermined bandwidth was measured pertaining to the amount of energy absorbed by the nucleate of the cells within the tissue sample. The amount of electromagnetic energy within the predetermined bandwidth was quantified.

DESCRIPTION OF THE PREFERRED EMBODIMENTS

The instant invention concept directs itself to an improved method of detecting cell malignancy in biological tissue. Denaturation are physical changes in DNA Which may result from extremes of pH; applied heat; decreases in dielectric constants of aqueous media; as well as exposure to urea, amides, and similar solutes. During denaturation of DNA, the covalent bonds are not broken, however, the double helical DNA structure unwinds and separates. Maintenance of the double-helical structure of DNA is responsive to hydrogen bonding between base pairs; as well as stacking interactions between successive bases. These are sometimes referred to as DNA bonding forces and when either of these forces are removed, the double helical structure will undergo a transition into a randomly looped form denoted as a denatured DNA.

Denaturation of DNA may be measured by the increase in electromagnetic energy absorption at a wavelength approximating 260.0 nm. Light absorption change has been termed as the hyperchromic effect. As is known, the purine and pyrimidine bases and their corresponding nucleotides absorb ultraviolet energy at a wavelength approximating 260.0 nm.

Normal double-stranded DNA absorbs less light at 260.0 nm than would be predicted from the summation of the light absorbed by the constituent mononucleotides. When double-stranded DNA is denatured by heating, there is a corresponding increase in the electromagnetic energy asborbed at 260.0 nm. The total electromagnetic energy absorption of fully denatured DNA is approximately equal to that of an equivalent number of corresponding free mononucleotides. The percentage increase in electromagnetic energy absorption at approximately 260.0 nm produced by heating a DNA sampled is generally related to its content of A-T base pairs and the higher proportion of A-T base pairs results in a greater increase in the electromagnetic energy absorption.

The less than additive light absorption by double-strand DNA molecules is called hypochromism and is believed to be due to the electronic interactions between the stacked bases in the double-helical structure which lowers the amount of light each residue may absorb. When the double-stand helical structure is in a disordered state, the bases will unstack and absorb as much electromagnetic energy as they would if they were present as free nucleotides.

DNA and its constituent bases have been found to provide a maximum absorbed ultraviolet light at wavelengths in the approximate range of 258.0–273.0 nm. It is known that individual bases of DNA have maximum absorption of electromagnetic energy at wavelengths as follows: Adenine, 260.4 nm; Thymine, 264.6 nm; Guanine, 271.3 nm; and, Cytosine, 265.5 nm. It has now been determined that cell nuclei also have a high absorptance of electromagnetic energy in this general ultraviolet wavelength range.

Since the base pairs are coiled into a double helix, much of the absorptive capacity of the bases is lost and the amount of light in the approximate wavelength of 260.0 nm decreases as has previously been noted in the hypochromic effect of impact DNA.

However, when hydrogen bonds are broken between base pairs of DNA, the bases are then free to move from the shadows of adjacent bases and exhibit full absorptive capacity. The degree of uncoiling of DNA prior to mytosis may thus be quantified.

As will be shown in following paragraphs, the degree of hydrogen bond destruction in DNA is directly related to the degree of malignant change in tissue. Thus, it is possible to now evaluate the activity of the cell in a tissue section and to identify cancerous specimens by its high nuclear absorptance.

In prior studies, the increased absorption of ultraviolet energy by cancer cell nuclei has been attributed to increased nucleic acid content of the nuclei. However, it is now believed that the breaking of the hydrogen bond between base pairs, which must occur for transcription and replication to take place, is a significant factor in quantitating the neoplastic potential of the epithelial cells. As will be understood, this concept is related to the previously described hypochromic effect of intact DNA.

Referring to the specific improved method of detecting cell malignancy in biological tissue, initially, a tissue sample was provided. In various experimental tests, human thyroid tissue obtained by surgical techniques were prepared by normal formalin fixation and paraffin embedding.

The tissue blocks were sectioned and then stained with a hematoxylin. Subsequent to the staining process, the tissue blocks were mounted on quartz slides with glycerin being used to affix the quartz cover slips. Prior to any experimental testing, all materials and compositions used were initially scanned and found not to absorb electromagnetic energy in any significant amount in the range of 260.0 nm.

The tissue samples or tissue blocks were impinged with electromagnetic energy within a predetermined electromagnetic energy bandwidth. A standard Zeiss microscope was used and fitted with quartz optics and adapted for ultraviolet microscopy. Optical filters were employed to selective wavelengths in the range of 255.0–265.0 nm.

The method steps include examining a substantially constant volume of nuclear material at all times. In order to maintain the substantially constant voluma of nuclear material being examined, the tissue blocks were sectioned to a substantially uniform thickness of 3.0 μm. Additionally, the aperture selection was in the range of 10.0 μm for the examination of the cell nuclei. Thus, the aperture selected was less in diameter than the magnified image of the nucleus being examined. Statistical significance of minor variations in the thickness of the sections was minimized by using the average absorption of a large number of cells from each section instead of an individual cell absorption value.

The aforementioned impingement of the tissue sample with electromagnetic energy within the predetermined electromagnetic energy bandwidth included the step of inserting the tissue sample under the microscope having the predetermined light or electromagnetic energy source. The predetermined light source was within the ultraviolet bandwidth of the electromagnetic energy spectrum and the light source was optically filtered prior to impingement on the tissue sample.

The step of filtering the electromagnetic energy included the step of intercepting the tissue sample with electromagnetic energy within the approximating wavelength bandwidth of 255.0–265.0 nm and in the preferred embodiment, intercepting the tissue sample with electromagnetic energy approximating 260.0 nm.

The amount of electromagnetic energy was measured within the predetermined bandwidth absorbed by the nucleate of the cells within the tissue sample. The step of measuring the amount of electromagnetic energy included the step of reflecting the electromagnetic energy from the tissue sample and passing the reflected electromagnetic energy through a subsequent optical filter approximating 260.0 nm filtering capacity.

Subsequent to the reflection step, the electromagnetic energy was collected in a photometer and the amount of electromagnetic energy within the predetermined bandwidth absorbed by the nucleate of the cells was quantified. The quantification included comparing the electromagnetic energy absorbed by the nucleate of the cells to the electromagnetic energy absorbed by nucleates of non-malignant cells.

Particular experimental tests were initiated utilizing the above described method steps. Human thyroid obtained by surgical techniques was used. The specimens prior to application of the steps as herein provided had previously been examined by pathologists using conventional histological methods and criteria for evaluation. Specimens were prepared by routine formalin fixation and paraffin embedding. Tissue blocks were sectioned, stained with hematoxylin and mounted on quartz slides with glycerin being used to affix the quarts cover slips.

The individual cell nuclei were visually located and the nuclear absorptance of each was measured and recorded. One hundred cells of each tissue section were examined and the mean absorptance and standard deviation were calculated for each section. In the overall test, twenty-four runs were completed and in the following tables I and II, the diagnosis is directed to the examination by pathologists using conventional histological methods and criteria for evaluation. Table I directs itself to the twenty-four runs made in order with Table II showing the data sorted by the mean nuclear absorptance at 260.0 nm.

TABLE I

NUCLEAR ABSORPTANCE OF THYROID EPITHELIUM AT 260.0 nm

| RUN NO. | DIAGNOSIS | MEAN ABSORPTANCE | STANDARD DEVIATION |
|---|---|---|---|
| 1 | Normal | 0.56 | 0.11 |
| 2 | Normal | 0.60 | 0.12 |
| 3 | Normal | 0.61 | 0.13 |
| 4 | Follicular adenoma | 0.78 | 0.33 |
| 5 | Follicular adenoma | 1.14 | 0.36 |
| 6 | Follicular adenoma (fetal type) | 1.20 | 0.15 |
| 7 | Follicular CA | 0.72 | 0.18 |
| 8 | Follicular CA (uninvolved area) | 0.72 | 0.22 |
| 9 | Metastasis of no. 8 to cervical node | 1.08 | 0.17 |
| 10 | Metastatis of no. 8 to bronchus | 1.05 | 0.23 |
| 11 | Follicular CA | 1.30 | 0.37 |
| 12 | Metastasis of no. 11 to cervical node | 1.30 | 0.27 |
| 13 | Papillary CA | 0.84 | 0.15 |
| 14 | Papillary CA | 0.89 | 0.19 |
| 15 | Metastasis of no. 14 to rec. lar. nerve | 1.01 | 0.22 |
| 16 | Papillary CA | 1.28 | 0.29 |
| 17 | Papillary CA (Follicular variant) | 0.87 | 0.18 |
| 18 | Papillary CA (Follicular variant) | 0.91 | 0.23 |
| 19 | Papillary CA (Follicular variant) | 1.15 | 0.19 |
| 20 | Metastasis of no. 19 to cervical nerve | 1.12 | 0.23 |
| 21 | Undifferentiated Large-cell CA | 0.93 | 0.40 |
| 22 | Anaplastic CA (Necrotic specimen) | 0.95 | 0.29 |
| 23 | Anaplastic CA | 1.13 | 0.28 |

TABLE I-continued

NUCLEAR ABSORPTANCE OF THYROID EPITHELIUM AT 260.0 nm

| RUN NO. | DIAGNOSIS | MEAN ABSORPTANCE | STANDARD DEVIATION |
|---|---|---|---|
| 24 | Anaplastic CA | 1.59 | 0.40 |

TABLE II

TABLE I DATA SORTED AS A FUNCTION OF INCREASING NUCLEAR ABSORPTANCE

| RUN NO. | DIAGNOSIS | MEAN ABSORPTANCE | STANDARD DEVIATION |
|---|---|---|---|
| 1 | Normal | 0.56 | 0.11 |
| 2 | Normal | 0.60 | 0.12 |
| 3 | Normal | 0.61 | 0.13 |
| 7 | Follicular CA | 0.72 | 0.18 |
| 8 | Follicular CA (uninvolved area) | 0.72 | 0.22 |
| 4 | Follicular adenoma | 0.78 | 0.33 |
| 13 | Papillary CA | 0.84 | 0.15 |
| 17 | Papillary CA (Follicular variant) | 0.87 | 0.18 |
| 14 | Papillary CA | 0.89 | 0.19 |
| 18 | Papillary CA (Follicular variant) | 0.91 | 0.23 |
| 21 | Undifferentiated large cell-CA | 0.93 | 0.40 |
| 22 | Anaplastic CA (Necrotic specimen) | 0.95 | 0.29 |
| 15 | Metastasis of no. 14 to rec. lar. nerve | 1.01 | 0.22 |
| 10 | Metastasis of no. 8 to bronchus | 1.05 | 0.23 |
| 9 | Metastasis of no. 8 to cervical node | 1.08 | 0.17 |
| 20 | Metastasis of no 19 to cervical node | 1.12 | 0.23 |
| 23 | Anaplastic CA | 1.13 | 0.28 |
| 5 | Follicular adenoma | 1.14 | 0.36 |
| 19 | Papillary CA (Follicular variant) | 1.15 | 0.19 |
| 6 | Follicular adenoma (Fetal type) | 1.20 | 0.15 |
| 16 | Papillary CA | 1.28 | 0.29 |
| 11 | Follicular CA | 1.30 | 0.37 |
| 12 | Metastasis of no. 11 to cervical node | 1.30 | 0.27 |
| 24 | Anaplastic CA | 1.59 | 0.40 |

By utilization of the above described method, it is seen from Tables I and II that when the volume of nuclear material is controlled, the nuclei of neoplastic cells absorb more light at the wavelength of 260.0 nm than those of normal cells. Thus, ultraviolet microspectrophotometry, using normally prepared tissue sections by the method steps as previously described may be used to quantitate the degree of malignant change in epithelial tissues.

Although this invention has been described in connection with specific steps and embodiments thereof, it will be described that various modifications other than those discussed above may be resorted to without departing from the spirit or scope of the invention. For example, equivalent method steps may be substituted for those specifically shown and described, certain features may be used independently of other features, and in certain cases, particular locations of elements may be reversed or interposed, all without departing from the spirit or scope of the invention as defined in the appended claims.

What is claimed is:

1. A method of detecting cell malignancy in biological tissue including the steps of:

(a) providing a tissue sample having a substantially constant thickness;

(b) impinging said tissue sample with electromagnetic energy within a predetermined electromagnetic energy bandwidth, said predetermined electromagnetic energy bandwidth being defined by optical filters having a specified approximating bandwidth of 255 to 265 nm;

(c) measuring the amount of electromagnetic energy within said predetermined bandwidth absorbed by a substantially constant volume portion of the nucleate from each of a plurality of individual cells within said tissue sample.

(d) quantifying said amount of electromagnetic energy within said predetermined bandwidth absorbed by said constant volume portions of said nucleate from each of said plurality of individual cells within said tissue sample, said quantification producing statistical data sets of both a mean and a standard deviation for said electromagnetic energy absorbed; and, (e) comparison of said statistical data sets produced form said quantification of said absorbed electromagnetic energy by said constant volume portions of said nucleate of said cells within said tissue sample with statistical data sets obtained from tissue samples predetermined to be non-malignant, said comparison providing the means to detect said cell malignancy.

2. The method of detecting cell malignancy as recited in claim 1 where said substantially constant tissue sample thickness approximates 3.0 um.

3. The method of detecting cell malignancy as recited in claim 1 where said statistical data sets are comprised of the mean value of the absorptance distribution for said plurality of said substantially constant volume portions of said nucleate and the standard deviation for said absorptance distribution.

4. The method of detecting cell malignancy as recited in claim 1 where the steps of impinging said tissue sample includes the steps of inserting said tissue sample under a microscope having a light source within said energy bandwidth.

5. The method of detecting cell malignancy as recited in claim 4 where said steps of impinging said tissue sample includes the step of reflecting electromagnetic energy having a wavelength approximating 260 nm from said tissue sample.

6. The method of detecting cell malignancy as recited in claim 1 where the step of providing a tissue sample includes the step of observing a single cell nucleate through a microscope.

7. The method of detecting cell malignancy as recited in claim 6 where the step of observing includes the step of selecting an aperture for said microscope smaller in diameter than the magnified image of the nucleus being observed.

8. The method of detecting cell malignancy as recited in claim 7 where said selected microscope aperture in combination with said substantially constant tissue sample thickness defines said substantially constant volume portion of said nucleus being observed.

9. The method of detecting cell malignancy as recited in claim 7 where the steps of measuring said amount of electromagnetic energy includes the steps of reflecting said electromagnetic energy from said tissue sample.

10. The method of detecting cell malignancy as recited in claim 9 where the step of reflecting is followed by the steps of passing said reflected electromagnetic energy through an optical filter approximating a 260 nm filter.

11. The method of detecting cell malignancy as recited in claim 9 where the step of reflecting is followed by the steps of collecting said reflected electromagnetic energy in a photometer.

12. A method of determining the grade of malignancy in tissue including the steps of:
   (a) impinging a constant volume portion of at least one cell nuclei with electromagnetic energy having an approximating bandwidth defined by optical filters having a specified approximating bandwidth of 255 to 265 nm;
   (b) measuring the amount of electromagnetic energy within said bandwidth absorbed by each of a plurality of said constant volume portion of each of said cell nuclei of said tissue; and,
   (c) comparing a mean and standard deviation of said amount of electromagnetic energy absorbed by each of said constant volume portions of said cell nuclei with absorption data obtained from a plurality of tissue samples, said plurality of tissue samples having been predetermined to provide examples of said grades of malignancy, said comparison providing the means for determining said grade of malignancy.

13. The method of determining the grade of malignancy as recited in claim 12 where said electromagnetic energy wavelength approximates 260.0 nm.

14. The method of determining the grade of malignancy as recited in claim 12 where the steps of measuring is preceded by the steps of detecting said electromagnetic energy reflected from said constant volume portion of said cell nuclei.

15. The method of determining the grade of malignancy as recited in claim 14 where the steps of detecting said reflected electromagnetic energy is preceded by the steps of filtering said electromagnetic energy prior to measuring said amount of electromagnetic energy absorbed by said constant volume portion of said cell nuclei.

* * * * *